United States Patent
Slepian et al.

(10) Patent No.: US 11,896,437 B2
(45) Date of Patent: Feb. 13, 2024

(54) DIGITAL REFLEX QUANTIZATION AND SIGNATURE ANALYSIS

(71) Applicant: Arizona Board of Regents on Behalf of the University of Arizona, Tucson, AZ (US)

(72) Inventors: Marvin J. Slepian, Tucson, AZ (US); Bruce M. Coull, Tucson, AZ (US); Hailey L. Swanson, Tucson, AZ (US); Rebecca C. Slepian, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 292 days.

(21) Appl. No.: 17/251,689

(22) PCT Filed: Jun. 12, 2019

(86) PCT No.: PCT/US2019/036809
§ 371 (c)(1),
(2) Date: Dec. 11, 2020

(87) PCT Pub. No.: WO2019/241412
PCT Pub. Date: Dec. 19, 2019

(65) Prior Publication Data
US 2021/0275152 A1   Sep. 9, 2021

Related U.S. Application Data

(60) Provisional application No. 62/684,179, filed on Jun. 12, 2018.

(51) Int. Cl.
*A61B 5/00*  (2006.01)
*A61B 5/11*  (2006.01)
(Continued)

(52) U.S. Cl.
CPC ............ *A61B 9/005* (2013.01); *A61B 5/1104* (2013.01); *A61B 5/395* (2021.01); *A61B 5/397* (2021.01);
(Continued)

(58) Field of Classification Search
CPC ......... A61B 9/00; A61B 9/005; A61B 5/1104; A61B 5/395; A61B 5/397; A61B 5/742;
(Continued)

(56) References Cited

U.S. PATENT DOCUMENTS

| | | |
|---|---|---|
| 5,263,489 A | 11/1993 | Johnson et al. |
| 2006/0135883 A1 | 6/2006 | Jonsson et al. |
| 2015/0109202 A1 | 4/2015 | Ataee et al. |
| 2017/0325704 A1 | 11/2017 | Powell et al. |

OTHER PUBLICATIONS

Burke, David, Simon C. Gandevia, and Brian McKeon. "The afferent volleys responsible for spinal proprioceptive reflexes in man." The Journal of physiology 339.1 (1983): 535-552. (Year: 1983).*

(Continued)

*Primary Examiner* — David J. McCrosky
*Assistant Examiner* — Nidhi N Patel
(74) *Attorney, Agent, or Firm* — Cozen O'Connor

(57) ABSTRACT

Systems and methods for digital reflex quantization and signature analysis. Movement of a stimulating device invoking a reflex response in an organism is captured as stimuli data. Electromyographic (EMG) of the reflex response is captured as EMG data. Movement resulting from the reflex response of a limb/appendage of the organism is captured as motion data. One or more of the stimuli data, the EMG data, and the motion data are analyzed to determine one or both of a motion signature and an EMG signature defining quantitative evaluation of the reflex response.

20 Claims, 11 Drawing Sheets

(51) Int. Cl.
    *A61B 5/395*     (2021.01)
    *A61B 5/397*     (2021.01)
    *A61B 9/00*     (2006.01)
    *G16H 20/30*     (2018.01)
    *G16H 50/30*     (2018.01)

(52) U.S. Cl.
    CPC ............. *A61B 5/742* (2013.01); *G16H 20/30* (2018.01); *G16H 50/30* (2018.01); *A61B 2562/0219* (2013.01)

(58) Field of Classification Search
    CPC ............ A61B 5/296; A61B 2562/0219; G16H 20/30; G16H 50/30; A61H 2230/60; A61H 39/04
    See application file for complete search history.

(56) References Cited

OTHER PUBLICATIONS

Lemoyne, Robert, et al. "Tendon reflex and strategies for quantification, with novel methods incorporating wireless accelerometer reflex quantification devices, a perspective review." Journal of Mechanics in Medicine and Biology 11.03 (2011): 471-513. (Year: 2011).*

Siegmund, Gunter P., et al. "Electromyography of superficial and deep neck muscles during isometric, voluntary, and reflex contractions." (2007): 66-77. (Year: 2007).*

PCT/US2019/036809 International Search Report and Written Opinion dated Aug. 30, 2019, 7 pp.

\* cited by examiner

DIGITAL REFLEX QUANTIZATION AND SIGNATURE ANALYSIS

RELATED APPLICATION

This Application claims priority to U.S. Patent Application No. 62/684,179, titled "Digital Reflex Quantization and Signature Analysis," filed Jun. 12, 2018, and incorporated herein by reference in its entirety.

BACKGROUND

Neurologic function is critical for function of organisms, particularly man and multicellular organisms. For man, we assess neurologic function using a range of physical examination approaches which we term the neurologic examination (neuro exam). In a neuro exam, reflexes, muscle function and strength, cranial nerves, and a range of other parameters are measured. Traditionally, most of these assessments are made using a range of simple tools such as a hammer, tuning fork, or needle, to assess reflexes, vibrational sense, or sensation, respectively. Reflexes are an excellent way to determine the integrity of the spinal cord and the peripheral nervous system. They can also be utilized to assess a range of neuro-muscular disorders as well as medical conditions or drug-altered states. The deep tendon reflex is stimulated via a peripheral strike, or the impartation of a force leading to stretch, typically on a tendon interacting with the muscle, and the associated reflex arc through the central nervous system at the spinal cord or brain and back to the muscle. The traditional means of assessing reflexes is to use a hammer, typically either of round hammer or tomahawk shape, where a tap or strike of a defined force is made on the tendon and reflex responses are typically graded using a zero through five scale, with 0: absent reflex; 1+: trace, or seen only with reinforcement; 2+: normal; 3+: brisk; 4+: non-sustained clonus; and 5+: sustained clonus. This assessment is largely subjective and semi-quantitative at best. Limitations of this approach include: variable induction of the response, subjective interpretation of movement, inter-observer variability, and inconsistencies in serial assessment.

Electronics today are pervasive throughout life and increasingly in medical diagnostics and therapeutics, and traditionally have been made out of stiff and rigid materials. In recent years, a trend has evolved to make electronic materials more flexible and frankly stretchable with the advent of stretchable interconnects and the blending and melding of these components—i.e. miniaturized semi-conductor devices, stretchable interconnects and stretchable polymeric materials. As such, a range of stretchable conformal constructs have been made possible.

SUMMARY

In the present invention, we describe the use of conformal sensors in a preferred embodiment, stretchable, made of stretchable electronic materials which may be applied to appropriate locations on a limb or part of a body region to both measure the movement associated with muscle contraction in the assessment of reflexes—deep, superficial and the like, as well as electromyographic (EMG) and other electric signals of the electro-mechanical coupling of the activity of the nervous system loop.

A first aspect of the present embodiments includes the realization that reflex assessment, typically assessed by a medical practitioner striking a patient and watching for the response, is not systematic or quantitative, and results are not reproducible. The present embodiments solve this problem by using wearable motion sensors to quantitatively measure movement of both a limb/appendage of patient and a stimulating device, as well as detecting EMG and other physiologic parameters. Advantageously, the present embodiments provide a more systematic, repeatable, and accurate way of determining reflexes in a quantitative reproducible way with greater sensitivity.

Stretchable electronics has allowed fabrication of conformal "wearable" motion sensors affording quantitative measurement of motion, its components, as well as EMG and additional physiologic parameters. A need and an opportunity exist for extracting signal information of these reflexes in terms of the frequency and rapidity of motion, the "signatures" that may occur of these motions, i.e., the signatures in the x, y, z, pitch, yaw, roll or six degrees of freedom space, as well as in the intensity and fatigue and other quantitative metrics, such as the time or lag from force (hammer) strike to initiation of muscle contraction, the strength of the EMG signal and similar quantitative variables of every aspect of the neurologic signaling and the muscular response, as well as the physical response associated with the limb to which the muscles are attached.

In one embodiment, a method is for digital reflex quantization and signature analysis. Movement of a stimulating device invoking a reflex response in an organism is captured as stimuli data. EMG of the reflex response is captured as EMG data. Movement resulting from the reflex response of a limb/appendage of the organism is captured as motion data. The stimuli data, the EMG data, and the motion data are analyzed to determine one or both of a motion signature and an EMG signature that forma quantitative evaluation of the reflex response.

In another embodiment, a system for digital reflex quantization and signature analysis includes a processor, a memory communicatively coupled with the processor, a first sensor configured to sense movement of a stimulating device invoking a reflex response in an organism, a second sensor configured to sense EMG of the reflex response, a third sensor configured to send movement resulting from the reflex response of a limb/appendage of the organism, and a reflex analyzer with machine readable instructions stored in the memory that, when executed by the processor, control the processor to: receive stimuli data from the first sensor; receive EMG data from the second sensor; receive motion data from the third sensor; and process the stimuli data, the EMG data, and the motion data to determine one or both of a motion signature and an EMG signature and to generate a quantitative evaluation of the reflex response.

Devices are described to evoke a reflex—either deep (tendon) or superficial which induce a defined stimulus—of defined intensity, force, frequency, depth or motion, or combination thereof, with defined and captured time—e.g., timing strike time, total stimulation time, time stamping and the like.

DETAILED DESCRIPTION OF THE EMBODIMENTS

Measurement of reflexes, deep tendon, superficial and the like, is a fundamental element of the neurologic exam performed by health personnel worldwide to evaluate upper vs. lower motor neuron function and disorders. Detection of reflex abnormalities is of particular value as changes may predate overt symptoms and signs of a given disorder. The most common reflexes tested are deep tendon reflexes (DTRs), subjectively assessed via limb/appendage movement and muscle contraction post hammer strike, rated on a 0-5 scale—as outlined above. This approach, while historic and universal, is fraught with limitation due to: poor performance technique, subjective interpretation of movement, inter-observer variability, and inconsistencies in serial assessment. Assessments of DTRs utilizing wearable sensors, able to assess limb/appendage 3D motion and muscle EMG, provide a means of quantization as well as defining motion and EMG "signatures" of a given reflex.

Figure 1:
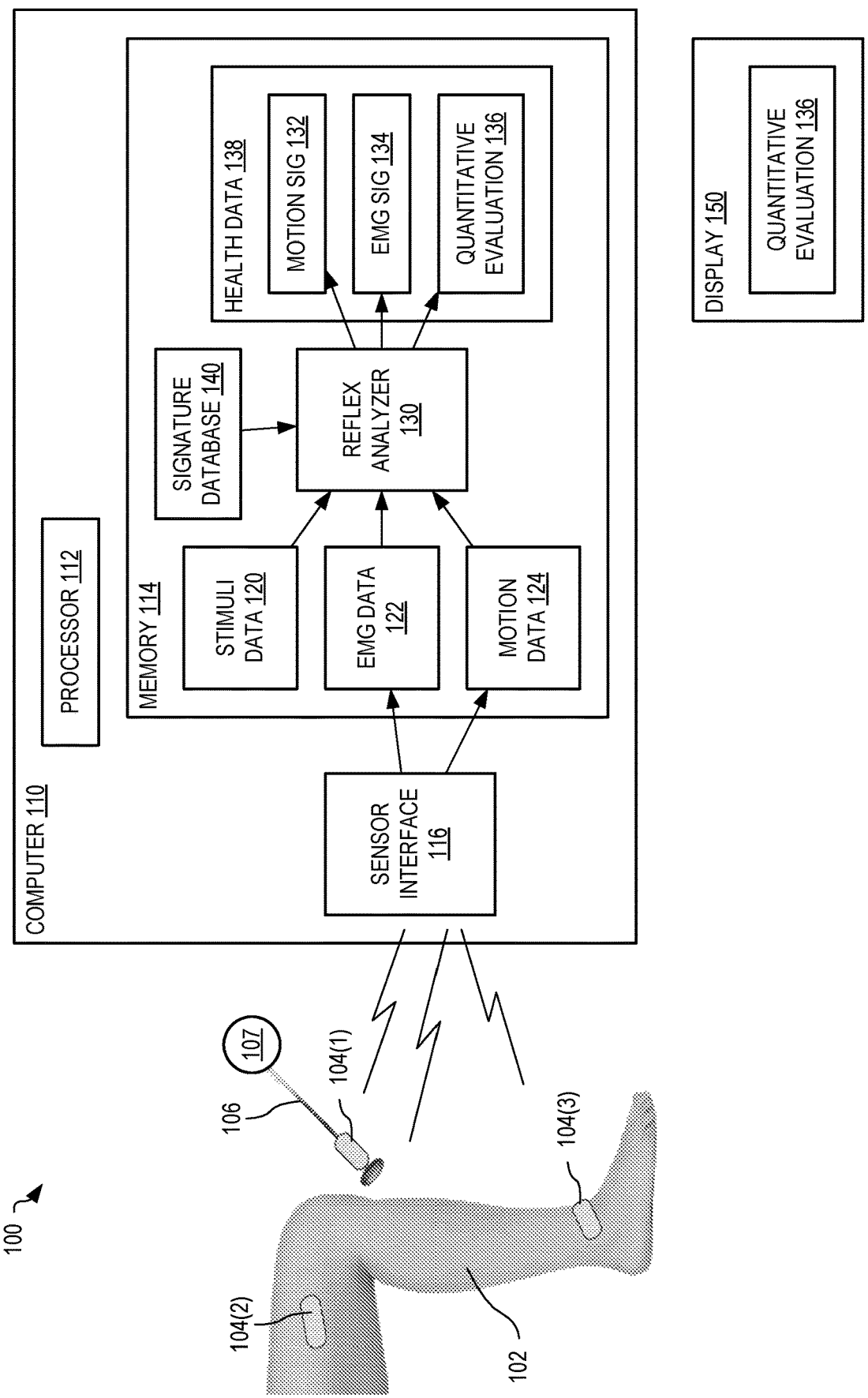
FIG. 1 is a block diagram of one system for digital reflex quantization and signature analysis, in an embodiment.

FIG. 1 shows one system 100 for digital reflex quantization and signature analysis. System 100 may be used for analyzing superficial reflexes for one or more of biceps, triceps, patellar and Achilles reflexes. System 100 includes a computer 110 with at least one processor 112 that is communicatively coupled with a memory 114 and a sensor interface 116. The sensor interface 116 may be wired and/or wireless and is communicatively coupled with a plurality of stretchable electronic sensors 104 (e.g., BioStamp™ from MC10 Inc.) that include tri-axial accelerometers for detecting motion and electrodes coupled with conditioning electronics for detecting EMG signals. As shown in FIG. 1, sensor 104(1) is applied to a stimulating device 106 (e.g., a reflex hammer) that is used to provide a stimulus or stimuli; sensor 104(2) is applied to a patient 102 to detect EMG signals of a muscle expected to respond to the stimuli applied by stimulating device 106; and sensor 104(3) is applied to the limb/appendage of patient 102 being moved by the muscle in response to the stimuli. By capturing both stimuli (sensor 104(1)) and response (sensors 104(2) and 104(3)), system 100 may coordinate stimuli strike vs reflex time lag, for example. Sensor 104(1) captures a strike by stimulating device 106, sensor 104(2) captures the EMG response of the muscle, and the sensor 104(3) captures the movement of the limb/appendage caused by the muscle. Sensors 104(1), 104(2), and 104(3) transmit (wired and/or wirelessly) the captured data to sensor interface 116 and the data is stored in memory 114 as stimuli data 120, EMG data 122, and motion data 124, respectively.

In one example of operation, sensor 104(3) is placed on the limb attached to or associated with the muscle. When the stimulating device 106 strikes the patellar tendon, the sensor 104(3) captures the movement of the distal leg as motion data 124, which is processed to generate motion signature 132 that provides an indication of the actuation of a proximate muscle in response to the physical stimuli. In certain embodiments, sensors 104(2) and (3) may form at least part of an array of sensors, for example configured with a fabric type material that allows the sensors to be 'worn' by patient 102. The array of sensors may form a network that is a smart patch, stamp, applique, fabric, mesh, band, stocking or glove-like configuration, or applied polymer apparatus, or that may be sprayed onto the patient 102. For example, sensors 104 may be configured as one or more of sock, a glove, a wraparound, and so on. Sensors 104, and/or the fabric may be permanent and reusable, may be disposable, and/or may be a kit.

Sensor 104(2) may be configured with electrodes and/or electrical sensors that sense EMG or other electrical signals associated with the muscle and that is simultaneously captured by the system 100, and may be synchronized with the electro-mechanical activation of the stimulating device 106.

Sensors 104 may each include one or more accelerometers and gyroscopes for detecting movement, including rotation in the x, y, and z-axes, and may sense accelerative force (G-force) and angular velocity (degrees/second) of the limb/appendage of patient 102. Each sensor 104 may also sense EMG, electrical potential of skeletal muscle, in millivolts. The captured EMG signals (e.g., EMG signature 134) reveal the time of the initial hammer strike vs. the time of the reflex and the physiologic constituent components of the reflex actuating. Each reflex produces a small lag time, or twitch interval, between the time of the initial stimulating device strike and the time the reflex occurred. This twitch interval may be quantitated (e.g., quantitatively defined/described) within both EMG signature 134 and motion signature 132.

A reflex analyzer 130, implemented as machine readable instructions stored in memory 114 and executed by processor 112, processes stimuli data 120, EMG data 122, and motion data 124 to generate a motion signature 132 and an EMG signature 134, each having a time reference with respect to a time of stimulation determined from stimuli data 120. In certain embodiments, reflex analyzer 130 generates a quantitative evaluation 136 of the captured reflex response. Defined, standard deep tendon reflexes are captured within the signatures 132 and 134 and demonstrate characteristic motion signatures, that may be assessed quantitatively, in both health and disease. The motion signature includes elements of one or components of the multiple degrees of freedom components of the motion, the quantitative depiction and rendition of this data, the three-dimensional integration and/or depiction of this data as a motion envelope; similar rendition and depiction of EMG and or other neuromuscular physiologic variables and their integration and three-dimensional depiction; as well as the time stamping and alteration of these over time. The signature may include and be defined by any and/or all of these elements.

In certain embodiments, stimulating device 106 may be automated such that computer 110 controls an actuator 107 that causes stimulating device 106 to create a reproducible force that's applied to the reflex of the patient 102. For example, actuator 107 and stimulating device 106 may include a housing that physically positions, relative to the patient 102, the stimulating device 106 to strike the appropriate location on the patient 102. Stimulating device 106 may thus be referred to as an intelligent stimulating device. For example, system 100 may include positioning apparatus that positions the stimulating device 106 to hit a tendon of the patient 102 at the correct location and with the appropriate force/velocity, wherein the computer 110 captures and synchronizes the data 120, 122, 124 from sensors 104 such that various reflex response parameters may be calculated from the resulting signatures 132, 134.

System 100 may also include a display 150 for displaying one or more of the motion signature 132, the EMG signature 134, and the quantitative evaluation 136. Display 150 may be part of computer 110 or a may be a separate device (e.g., a monitor, a tablet computer, a smartphone, etc.).

Sensors 104(1)-(3) and corresponding data 120, 122, 124 allow quantitation of movement (dimension data), acceleration, muscle contraction and timing of reflex responses. Motion signature 132 and EMG signature 134, generated readily, allow quantitation of component elements and intervals associated with these signals. Trials indicate that the use of sensors 104 allow reproducibility of signatures 132 and 134 and thereby confidence of quantitative evaluation 136 determined therefrom. Accordingly, the use of system 100 for evaluating reflexes in patient 102 provides standardization, reduced inter-observer variability, and meaningful serial assessment.

Signatures 132 and 134 generated by reflex analyzer 130 allow detection of reflex abnormalities, and quantitative evaluation 136 indicates changes in reflex response, for example as compared to previously captured signatures of patient 102, or as compared to standardized signatures. Such changes in reflex response may predate overt symptoms and signs of a given disorder. For example, previously captured signatures of patient 102 and/or standardized signatures may be stored within a signature database 140 to allow comparison by reflex analyzer 130. In another example, database 140 may store signatures of healthy reflex responses and signatures of reflex responses corresponding to different diseases and/or disorders. Accordingly, through use of system 100, signatures 132, 134 may be matched to reference signatures to diagnose the disorder significantly earlier for patient 102 as compared to conventional subjective reflex evaluations. Sensors 104 are each conformal, adherent, wearable sensing electronics that readily allow capture of both motion (displacement, velocity and acceleration) as well as EMG signals of deep tendon reflexes.

The above signature, stored in a database may be systematically analyzed and refined over time to further elicit more characteristic signatures of a given state, condition, disease or pharmacologically induced state. This may be accomplished through repetitive processing of inputted signature data, using machine learning, big data techniques, as described in U.S. patent application Ser. No. 15/746,767, titled "Systems and Methods for Analyzing Healthcare Data", filed Jan. 22, 2018.

The signature data—both individual and refined via machine learning may be integrated into the electronic health record—such as EPIC or Cerner.

System 100 provides standardization, reduced inter-observer variability and meaningful serial assessment of deep tendon reflexes. System 100 may also be used to define signatures/intervals of additional reflexes, identify differences between normal reflexes and those associated with disease pathologies, and define patterns/quantitative element alterations with exercise, fatigue, and medications. For example, system 100 may detect one or both of hypo and hyperthyroidism, which are examples of diseases where reflexes change, and where such change may be detected within signatures 132, 134 and indicated within quantitative evaluation 136.

Figure 2:
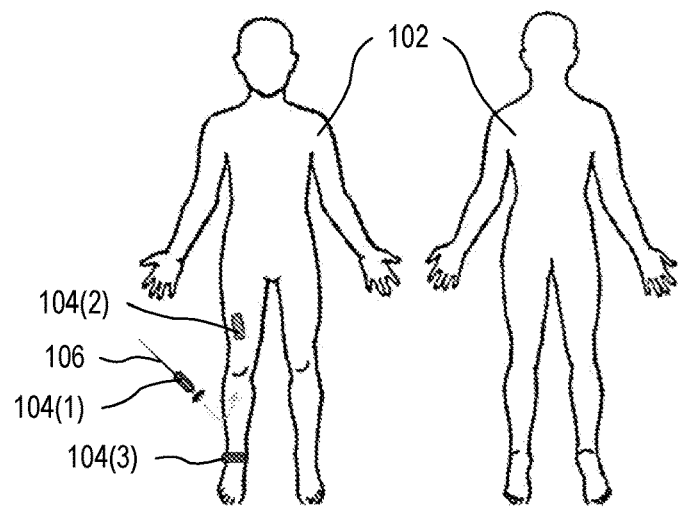
FIG. 2 is a schematic diagram illustrating, in an example scenario, placement of sensors on a patient for digital reflex quantization and signature analysis of a Patellar reflex response.
Figure 3:
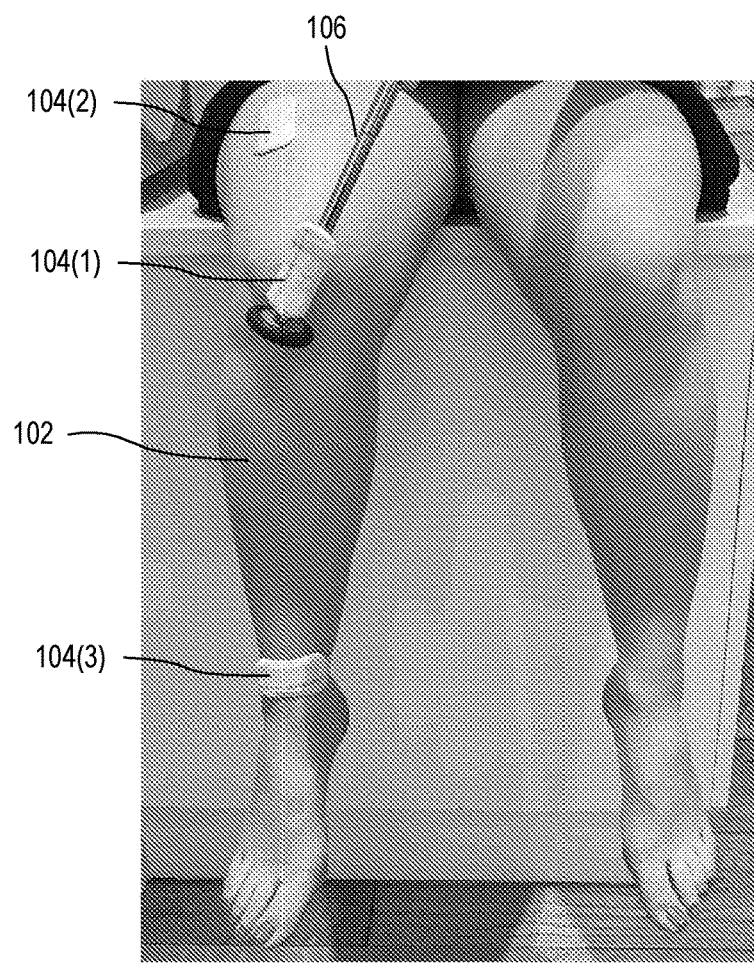
FIG. 3 is photograph illustrating, in an example scenario, placement of sensors on a patient for digital reflex quantization and signature analysis of a patellar reflex response.
Figures 4A, 4B:
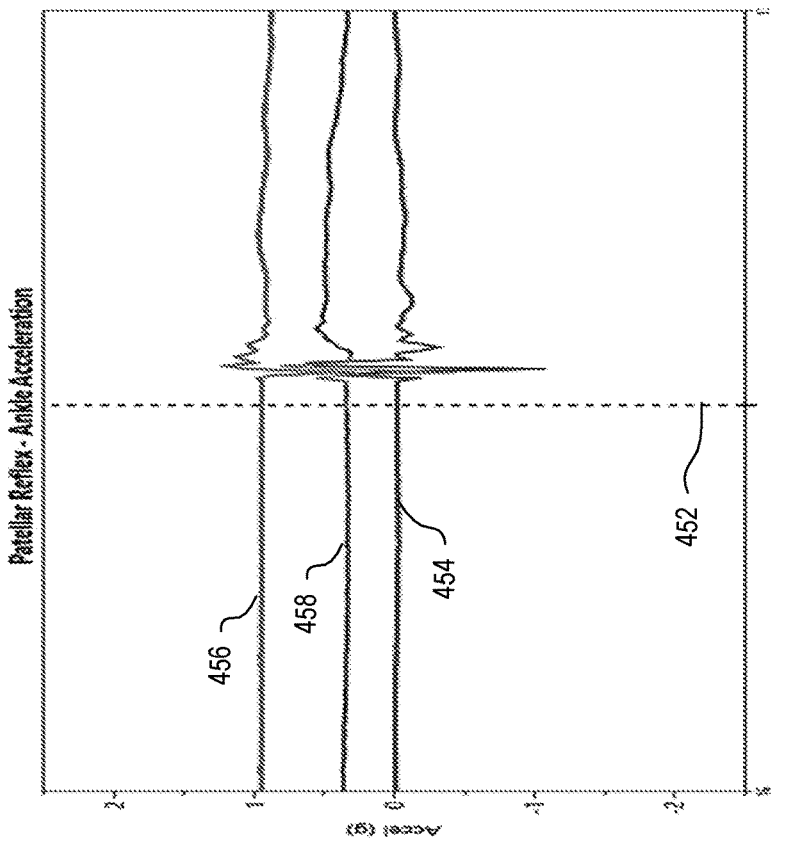
FIG. 4A shows an example EMG signature for a patellar reflex response.
FIG. 4B shows an example motion signature for the patellar reflex response of FIG. 4A.

FIG. 2 is a schematic illustrating placement of sensors on a patient for digital reflex quantization and signature analysis of a Patellar reflex response. FIG. 3 is photograph illustrating placement of sensors on a patient for digital reflex quantization and signature analysis of the Patellar reflex response. As shown in FIGS. 2 and 3, sensor 104(1) is configured with the stimulating device 106, sensor 104(2) is configured to sense EMG of the quadriceps muscles, and sensor 104(3) is configured at an ankle of the corresponding leg of patient 102 to sense motion. FIG. 4A shows an example EMG signature 400 with a curve 404 representing EMG signature 134. FIG. 4B shows an example motion signature 450 for the patellar reflect of FIG. 4A with three curves 454, 456, and 458 representing acceleration in X, Y, and Z directions, respectively, of motion signature 132 for patient 102. Dashed lines 402 and 452 indicate a common normalized time that provides a reference between signatures 400 and 450.

Figure 5:
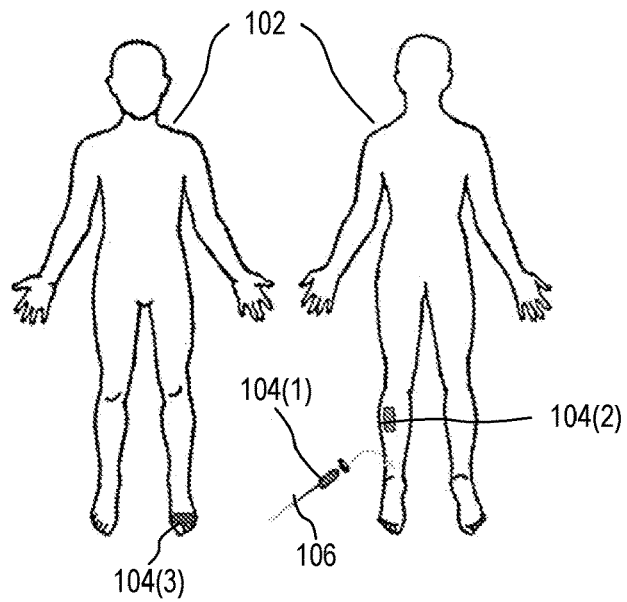
FIG. 5 is a schematic illustrating, in an example scenario, placement of sensors on a patient for digital reflex quantization and signature analysis of an Achilles reflex response.
Figure 6:
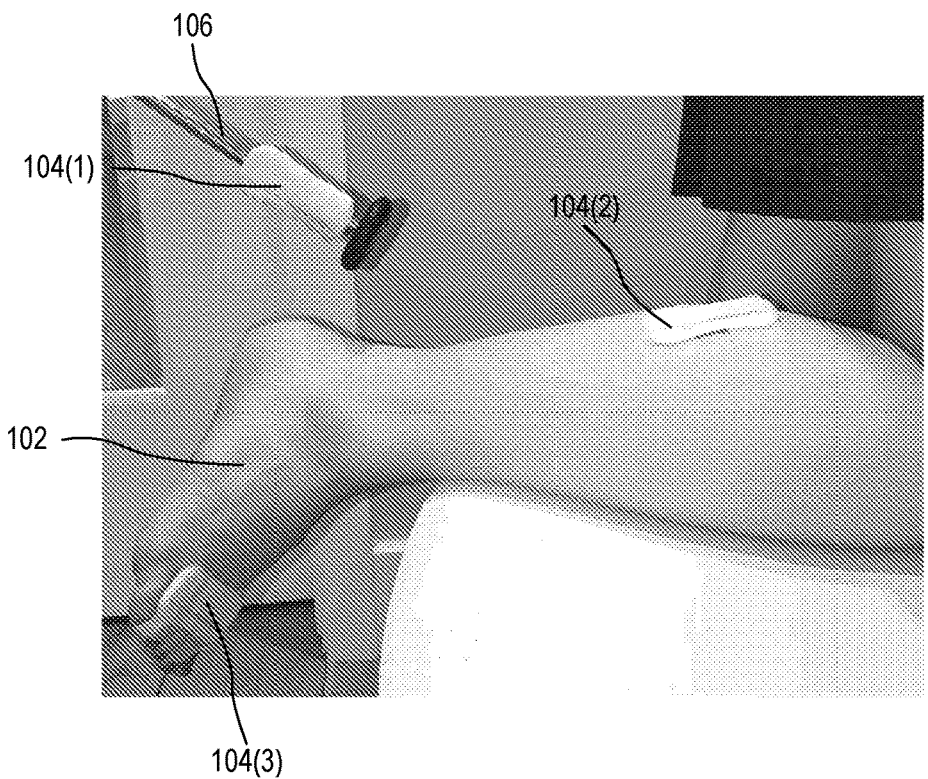
FIG. 6 is photograph illustrating, in an example scenario, placement of sensors on a patient for digital reflex quantization and signature analysis of an Achilles reflex response.
Figure 7B:
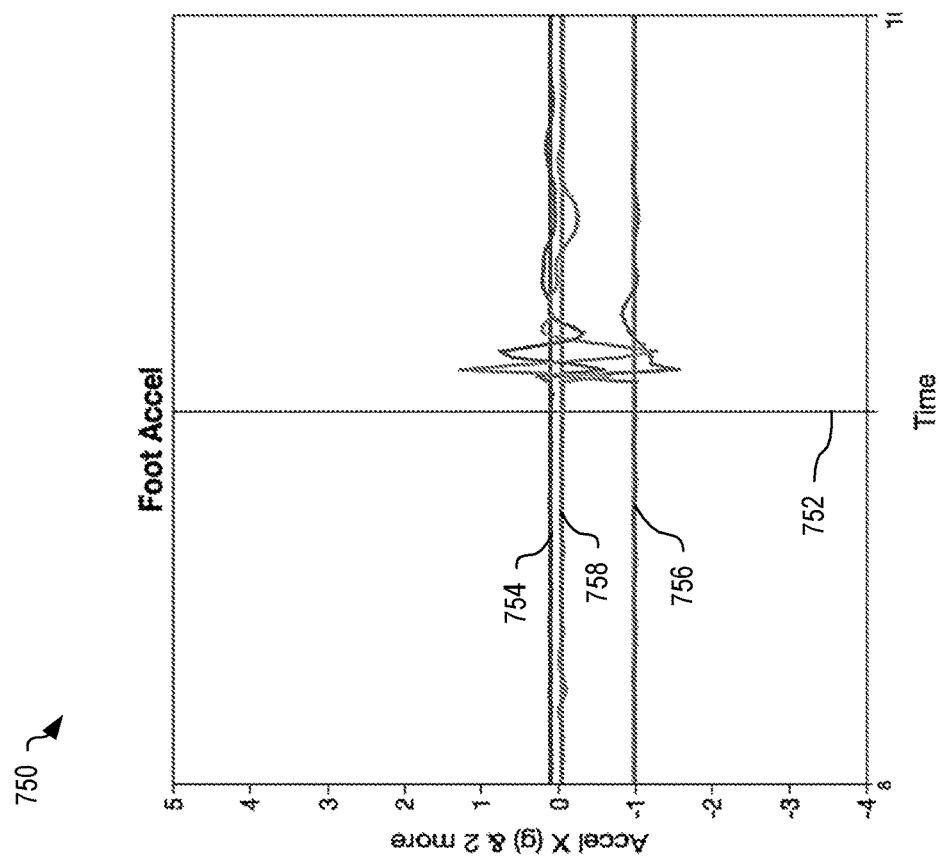
FIG. 7B shows an example motion signature for the Achilles reflex response of FIG. 7A.
Figure 7A:
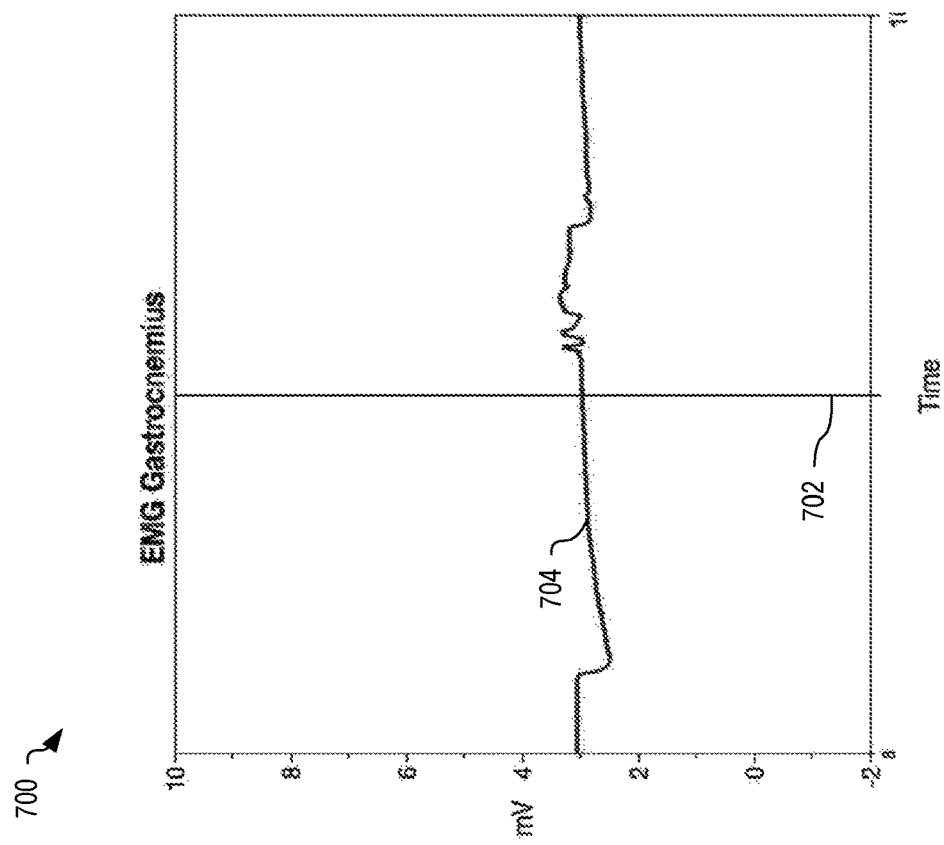
FIG. 7A shows an example EMG signature for an Achilles reflex response.

FIG. 5 is a schematic illustrating placement of sensors 104 on patient 102 for digital reflex quantization and signature analysis of an Achilles reflex response. FIG. 6 is photograph illustrating placement of sensors 104 on patient 102 for digital reflex quantization and signature analysis of the Achilles reflex response. As shown in FIGS. 5 and 6, sensor 104(1) is configured with the stimulating device 106, sensor 104(2) is configured to sense EMG of the calf muscle, and sensor 104(3) is configured at an ankle of the corresponding leg of patient 102 to sense motion. FIG. 7A shows an example EMG signature 700 for an Achilles reflex response with a curve 704 representing signature 700. FIG. 7B shows an example motion signature 750 for the Achilles reflex response of FIG. 7A with three curves 754, 756, and 758 representing acceleration in X, Y, and Z directions, respectively, of motion signature 132 for patient 102. Dashed lines 702 and 752 indicate a common normalized time that provides a reference between signatures 700 and 750.

Figure 8:
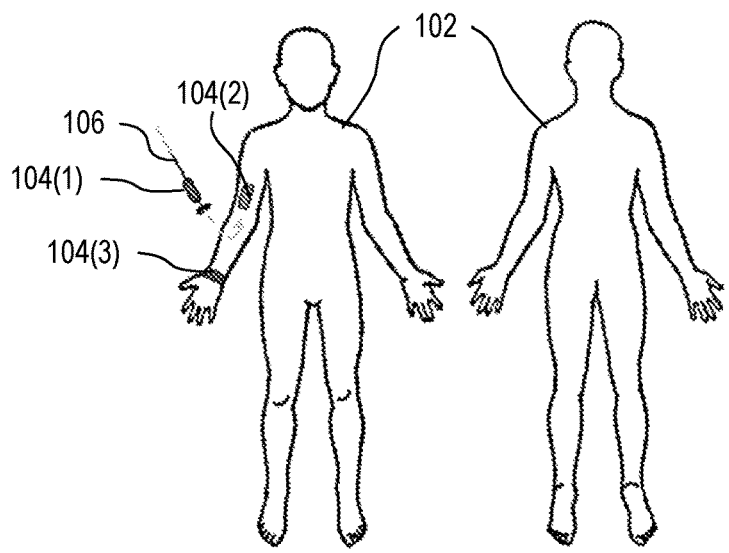
FIG. 8 is a schematic illustrating, in an example scenario, placement of sensors on a patient for digital reflex quantization and signature analysis of a biceps reflex response.
Figure 9:
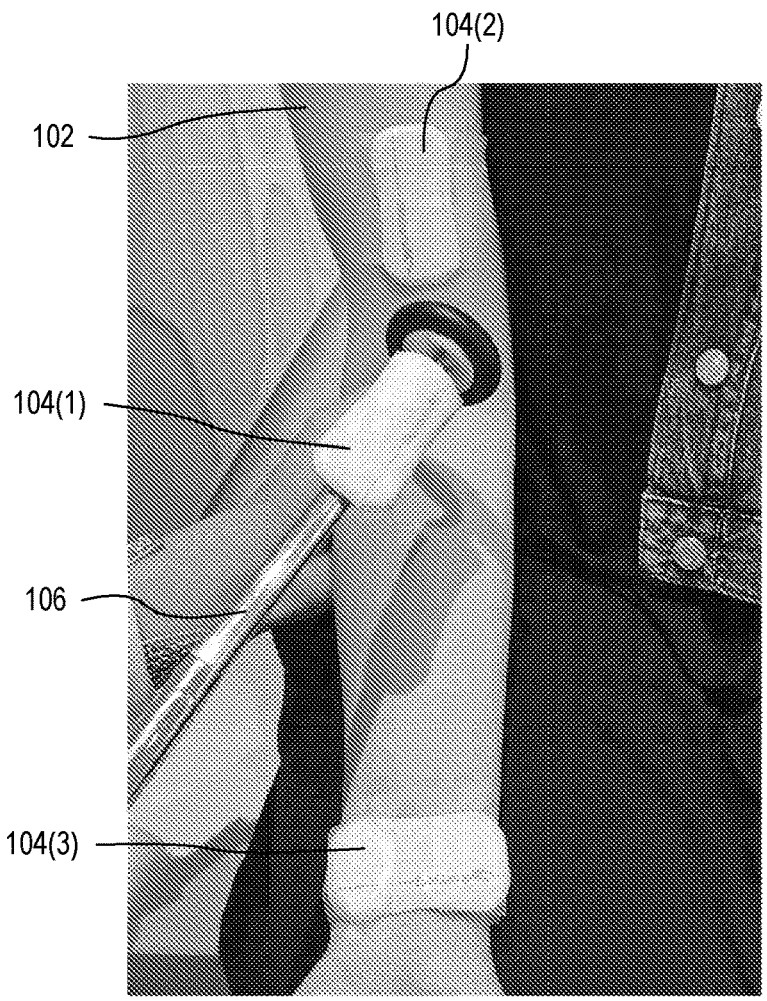
FIG. 9 is photograph illustrating, in an example scenario, placement of sensors on a patient for digital reflex quantization and signature analysis of a biceps reflex response.
Figure 10B:
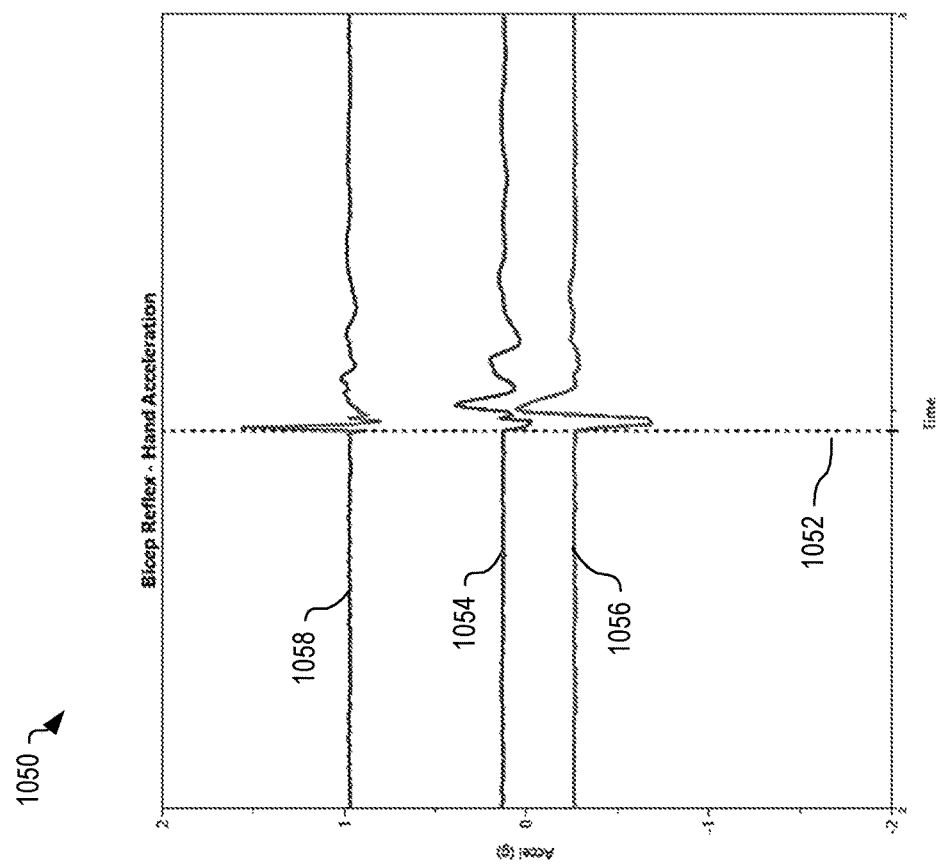
FIG. 10B shows an example motion signature for the biceps reflex response of FIG. 10A.
Figure 10A:
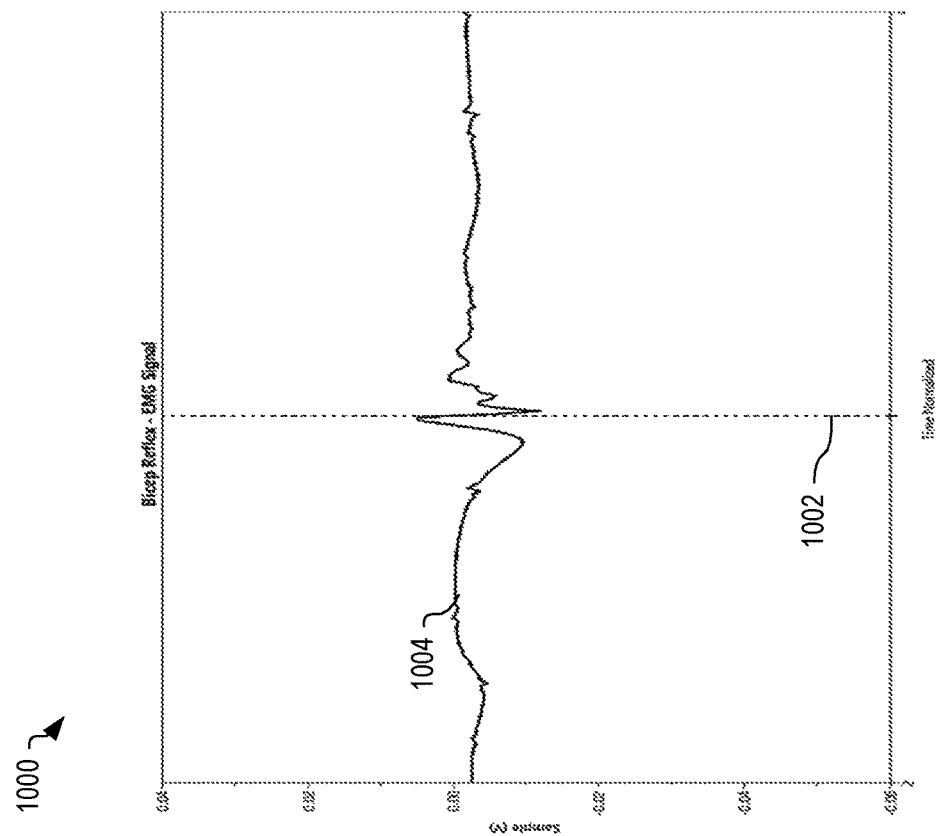
FIG. 10A shows an example EMG signature for a biceps reflex response.

FIG. 8 is a schematic illustrating placement of sensors 104 on patient 102 for digital reflex quantization and signature analysis of a biceps reflex response. FIG. 9 is photograph illustrating placement of sensors 104 on patient 102 for digital reflex quantization and signature analysis of the biceps reflex response. As shown in FIGS. 8 and 9, sensor 104(1) is configured with the stimulating device 106, sensor 104(2) is configured to sense EMG of the biceps muscle, and sensor 104(3) is configured at a wrist of the corresponding arm of patient 102 to sense motion. FIG. 10A shows an example EMG signature 1000 for a biceps reflex response with a curve 1004 representing signature 1000. FIG. 10B shows an example motion signature 1050 for the biceps reflex response of FIG. 10A with three curves 1054, 1056, and 1058 representing acceleration in X, Y, and Z directions, respectively, of motion signature 132 for patient 102. Dashed lines 1002 and 1052 indicate a common normalized time that provides a reference between signatures 1000 and 1050.

Figure 11:
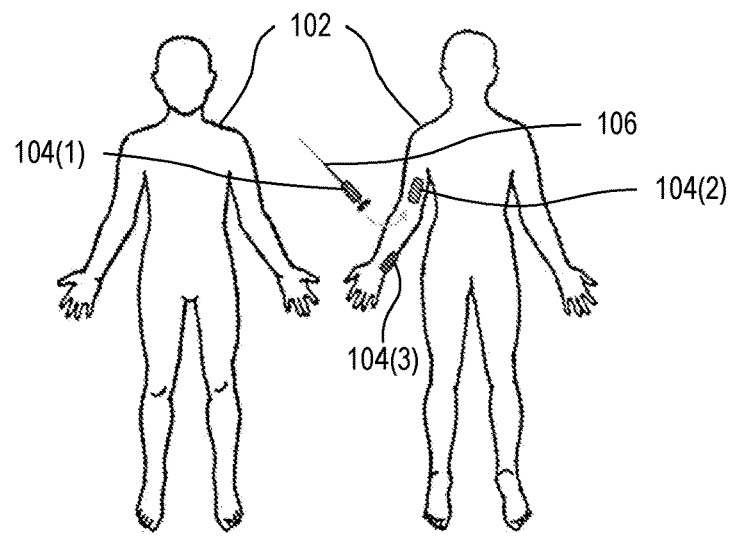
FIG. 11 is a schematic illustrating, in an example scenario, placement of sensors on a patient for digital reflex quantization and signature analysis of a triceps reflex response.
Figure 12:
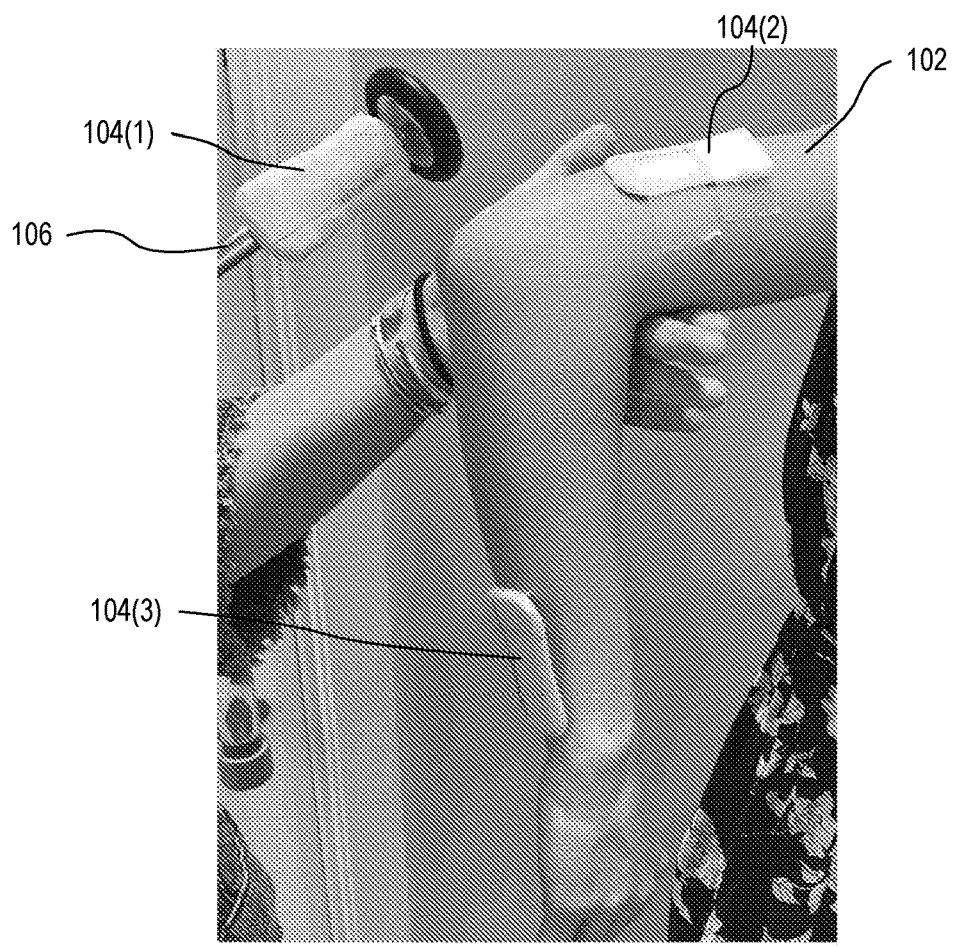
FIG. 12 is photograph illustrating, in an example scenario, placement of sensors on a patient for digital reflex quantization and signature analysis of a triceps reflex response.
Figure 13B:
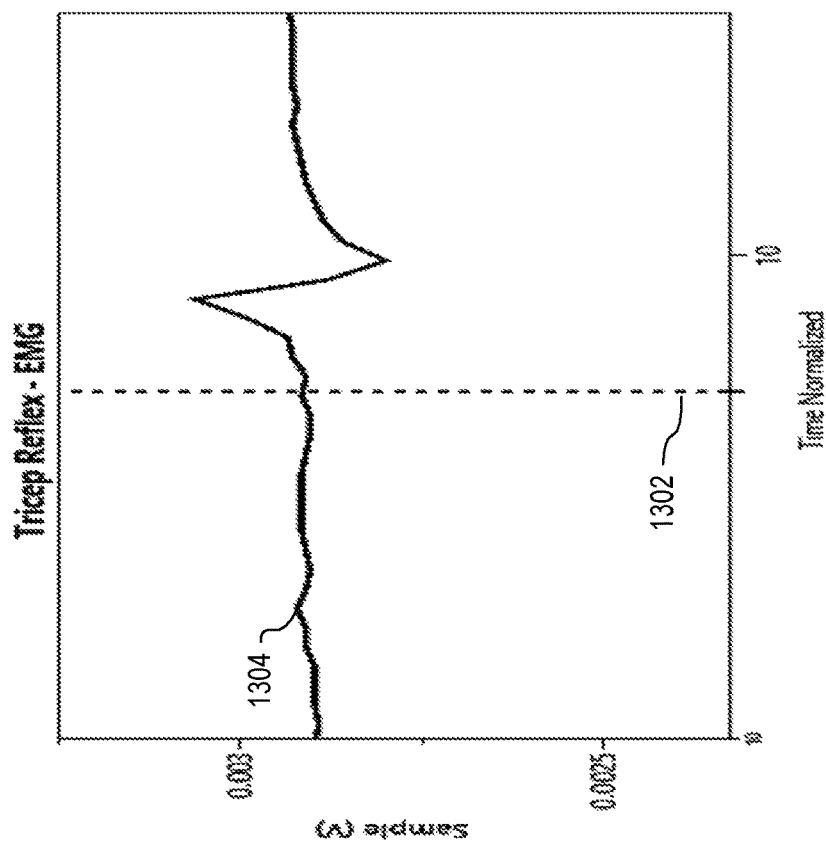
FIG. 13B shows an example motion signature for the triceps reflex response of FIG. 13A.
Figure 13A:
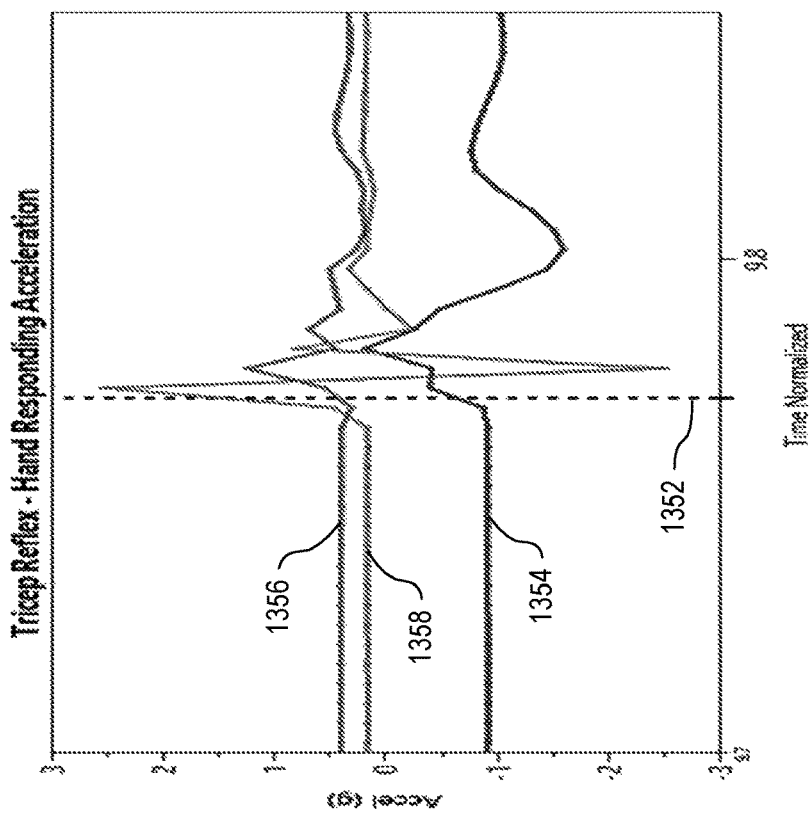
FIG. 13A shows an example EMG signature for a triceps reflex response.

FIG. 11 is a schematic illustrating placement of sensors 104 on patient 102 for digital reflex quantization and signature analysis of a triceps reflex response. FIG. 12 is photograph illustrating placement of sensors 104 on patient 102 for digital reflex quantization and signature analysis of the triceps reflex response. As shown in FIGS. 11 and 12, sensor 104(1) is configured with the stimulating device 106, sensor 104(2) is configured to sense EMG of the triceps muscle, and sensor 104(3) is configured at a wrist of the corresponding arm of patient 102 to sense motion. FIG. 13A shows an example EMG signature 1300 for a triceps reflex response with a curve 1304 representing signature 1300. FIG. 13B shows an example motion signature 1350 for the triceps reflex response of FIG. 13A with curves lines 1354, 1356, and 1358 representing acceleration in X, Y, and Z directions, respectively, of motion signature 132 for patient 102. Dashed lines 1302 and 1352 indicate a common normalized time that provides a reference between signatures 1300 and 1350.

Figure 14:
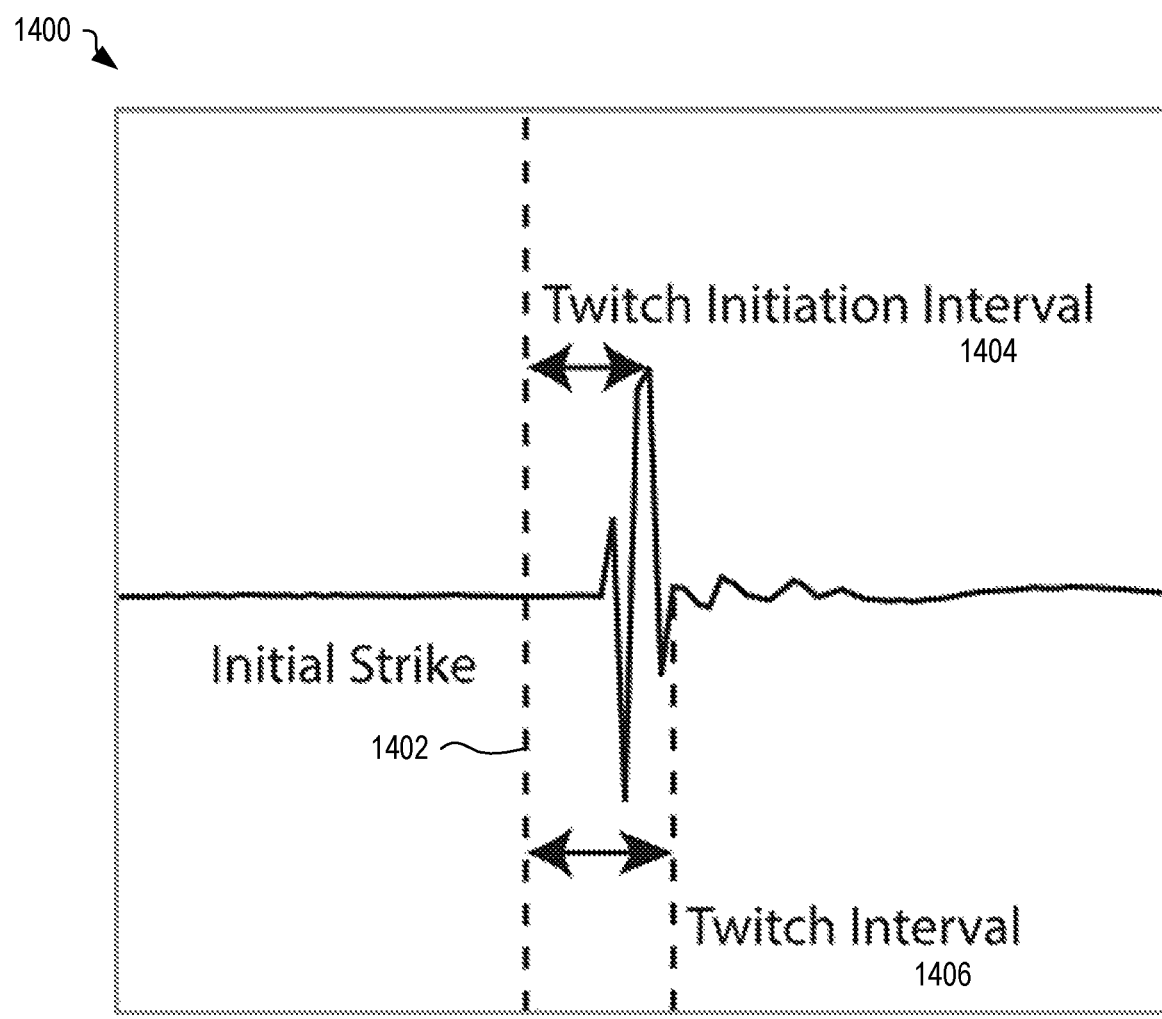
FIG. 14 shows an example EMG response with key features identified.

FIG. 14 shows an example EMG response 1400 with key features identified. An initial strike time 1402 (shown as a dashed line) indicates relative timing of when stimulating device 106 struck a tendon of patient 102. A twitch initiation interval 1404 starts at initial strike time 1402 and represents a period for muscle activation and a twitch interval 1406 starts at initial strike time 1402 and represents a duration of the response.

In analyzing these signatures 132, 134, 400, 450, 700, 750, 1000, 1050, 1300, 1350, and 1400, it is clear that a defined type of movement occurs for each affected limb or each affected reflex and as such, a particular x, y, z, pitch, yaw, roll movement signature is obtained for a given reflex tested. It has been demonstrated that differences in these signatures occur for different limbs, for patients of different age, and for patients on different medications, where they may be hyperreflexive or hyporeflexic, and similarly varying for different diseases, thereby allowing system 100 to detect these abnormalities and thereby predict the corresponding disease.

Reflex analyzer 130 may also determine time parameters from the data 120, 122, and 124 and/or the signatures 132 and 134 signals, such as the time or the lag from initiation of muscle strike to movement, that's a variable. Reflex analyzer 130 may determine the peak width and height of the movement signal, the time from the strike to the EMG contraction, and may determine similar patterns in EMG signature 134, such as a pattern of the EMG contraction or a height. System 100 may generate one or more graphs on display 150 for example, that may allow graphical analysis including fast Fourier transform or other analyses to determine additional information from the data and/or signatures. System 100 effectively connects stimulating device 106 and sensors 104, both on the movement limb as well as on the involved muscle which may be on opposite sides of a joint.

In certain embodiments, system 100 may upload the captured data 120, 122, and 124, signatures 132 and 134, and quantitative evaluation 136 to the cloud for further analysis and/or storage (e.g., as health data 138), and may have further ability to process and store the data within computer 110. In certain embodiments, system 100 may include one or more imaging apparatuses (e.g., a camera, etc.) for capturing visual information of the reflex response. In certain embodiments, display 150 is a heads-up display or other graphic medical storage and display device. In certain embodiments, system 100 may be used to measure muscle strength. Rather than using stimulating device 106 to strike a tendon, system 100 may include a device (or instruct an individual) to apply a force to an affected limb, thinking of the fulcrum of the limb versus the muscle. The patient is instructed to voluntarily raise or lower the affected limb while sensor 104 captures EMG data of the muscle to generate an EMG signature and motion data to generate a motion signature, and forces (using a force sensors) of contraction to determine quantitative measurements of resistance pressure and motion. In another embodiment, sensor 104 may be configured on a physician or health care provider and used to sense resistive force applied by that person, such that system 100 may integrate all data to form comprehensive signatures 132, 134 and quantitative evaluation 136. Accordingly, system 100 provides an assessment of neurologic function of patient 102, and provides specific assessment of particular reflex responses.

Figure 15:
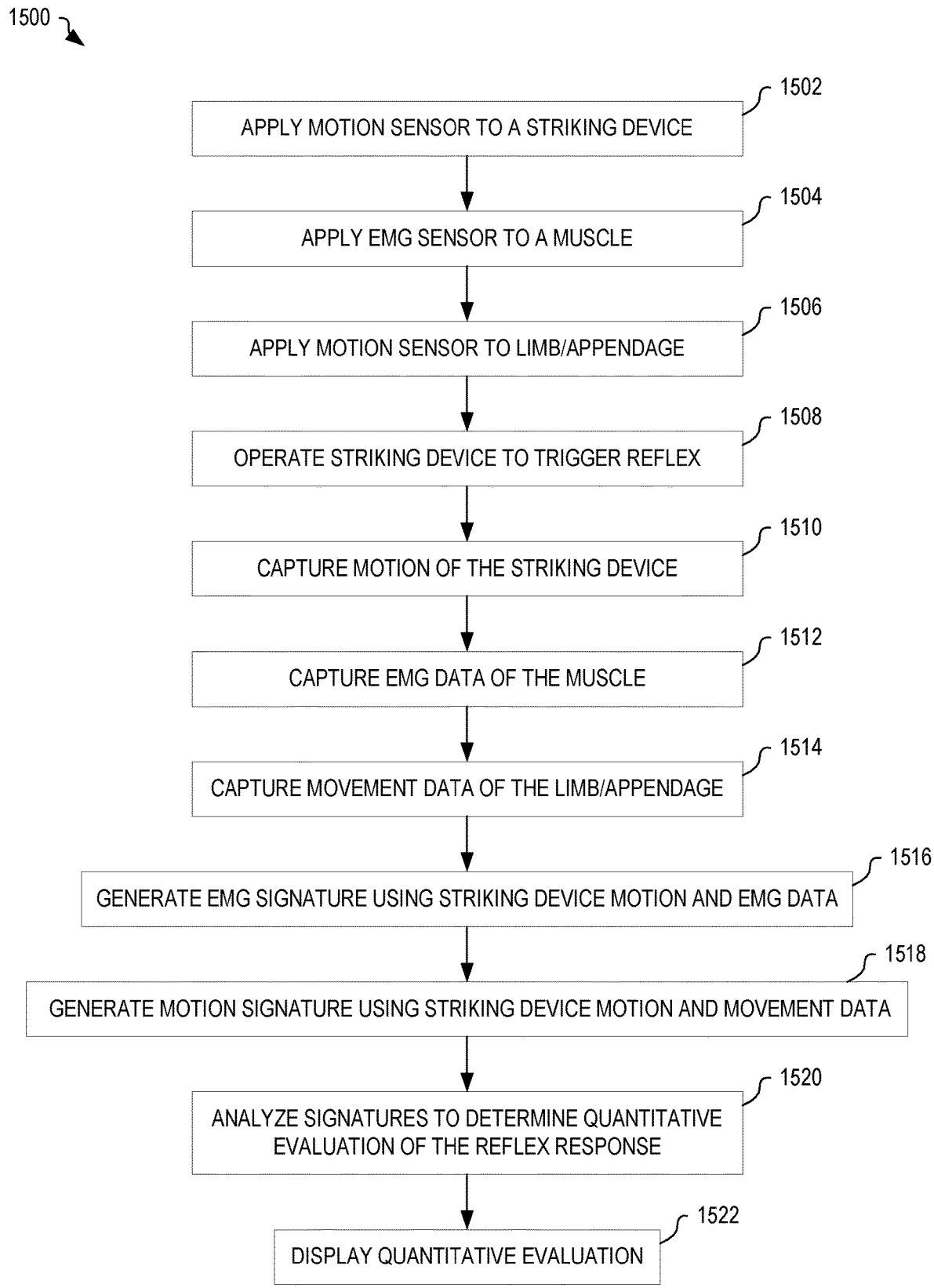
FIG. 15 is a flowchart illustrating one example method for digital reflex quantization and signature analysis.

FIG. 15 is a flowchart illustrating one example method 1500 for digital reflex quantization and signature analysis. Method 1500 is for example implemented at least in part within sensors 104 and computer 110 of FIG. 1.

In optional step 1502, method 1500 applies a motion sensor to a striking device. In one example of step 1502, sensor 104(1) is applied to stimulating device 106. In step 1504, method 1500 applies an EMG sensor to a muscle. In one example of step 1504, sensor 104(2) is applied to the quadriceps muscle of the leg of patient 102. In step 1506, method 1500 applies a motion sensor to a corresponding limb/appendage. In one example of step 1506, sensor 104(3) is applied to the corresponding ankle of patient 102.

In step 1508, method 1500 operates the striking device to trigger a reflex. In one example of step 1508, a doctor uses stimulating device 106 to strike a patellar tendon of patient 102. In another example of step 1508, computer 110 controls an actuator to cause stimulating device 106 to strike the patellar tendon of patient 102. In step 1510, method 1500 captures motion of the striking device. In one example of step 1510, computer 110 receives data from sensor 104(1) of captured motion of stimulating device 106 and stores it as stimuli data 120 within memory 114. In step 1512, method 1500 captures EMG data of the muscle. In one example of step 1512, computer 110 receives data from sensor 104(2) and stores the data as EMG data 122 within memory 114. In step 1514, method 1500 captures movement data of the limb/appendage. In one example of step 1514, computer 110 receives data from sensor 104(3) and stores the data as motion data 124 within memory 114.

In step 1516, method 1500 generates an EMG signature using striking device motion and EMG data. In one example of step 1516, reflex analyzer 130 processes stimuli data 120 and EMG data 122 to generate EMG signature 134. In step 1518, method 1500 generates a motion signature using striking device motion and movement data. In one example of step 1518, reflex analyzer 130 processes stimuli data 120 and motion data 124 to generate motion signature 132. In step 1520, method 1500 analyzes signatures to determine a quantitative evaluation of the reflex response. In one example of step 1520, reflex analyzer 130 generates quantitative evaluation 136 by analyzing one or both of motion signature 132 and EMG signature 134 in view of signature database 140. In step 1522, method 1500 displays the quantitative evaluation. In one example of step 1522, reflex analyzer 130 displays quantitative evaluation 136 on display 150. Steps of method 1500 may be performed in a different order without departing from the scope hereof. For example, step 1504 may be performed before or concurrently with step 1502, step 1512 may be performed before or concurrently with step 1510, and step 1518 may be performed before or concurrently with step 1516. In certain embodiments, some steps of method 1500 may be omitted. For example, in embodiments where EMG signature is not generated, steps 1504, 1512, and 1516 may be omitted.

In the examples described herein, stimulating device 106 is represented as a hammer. However, stimulating device 106 may be other types of stimulator, such as one or more of a tuning fork, a needle, and a feather or soft material. Accordingly, the stimulation is not limited to provoking deep tendon reflexes, but may also include noxious or tactile stimulation of the skin, such as tickling, to invoke other types of superficial reflex. In certain embodiments, stimulating device 106 and sensor 104(1) may be combined to form a smart stimulator that may be controlled by computer 110 to apply stimulation at a desired intensity, repeat count, frequency, and so on. The smart stimulator may communicate with one or both of sensors 104(2) and 104(3) to define and coordinate timing of the stimulation and sensing of the reflex response, as described above.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween. In particular, the following embodiments are specifically contemplated, as well as any combinations of such embodiments that are compatible with one another:

(A) A method for digital reflex quantization and signature analysis, includes: capturing, as stimuli data, movement of a stimulating device invoking a reflex response in an organism, capturing, as electromyographic (EMG) data, EMG of the reflex response, capturing, as motion data, movement resulting from the reflex response of a limb/appendage of the organism, and analyzing the stimuli data, the EMG data, and the motion data to determine one or both of a motion signature and an EMG signature comprising quantitative evaluation of the reflex response.

(B) In the method denoted as (A), the step of analyzing may include comparing one of the motion signature and the EMG signature to a corresponding one of a previously captured motion signature and a previously captured EMG signature to generate the quantitative evaluation of the reflex response.

(C) In either of the methods denoted as (A) and (B), the step of analyzing may include comparing one of the motion signature and the EMG signature to a corresponding reference motion signature or reference EMG signature to generate the quantitative evaluation of the reflex response.

(D) Any of the methods denoted as (A)-(C) may further include matching one or both of the EMG signature and the motion signature to reference signatures corresponding to reflex responses for one or more diseases and/or disorders to diagnose a disease and/or disorder of the organism.

(E) In any of the methods denoted as (A)-(C), the motion signature may define a three-dimensional movement of the limb/appendage and the stimuli data defining a time of stimulation, the motion signature and the EMG signature being referenced to the time of stimulation.

(F) In any of the methods denoted as (A)-(E), the quantitative evaluation may be based at least in part upon three-dimensional acceleration of the limb/appendage quantitatively measured by at least three accelerometers configured with the limb/appendage.

(G) In any of the methods denoted as (A)-(F), the stimuli data may include three-dimensional acceleration measurements of movement of the stimulating device.

(H) Any of the methods denoted as (A)-(G), may further include controlling an actuator to generate the movement of the stimulating device to invoke the reflex response.

(I) Any of the methods denoted as (A)-(H), may further include displaying the quantitative evaluation of the reflex response to indicate health of the organism.

(J) A system for digital reflex quantization and signature analysis includes: a processor, a memory communicatively coupled with the processor, a first sensor configured to sense movement of a stimulating device invoking a reflex response in an organism, a second sensor configured to sense EMG of the reflex response, a third sensor configured to sense movement resulting from the reflex response of a limb/appendage of the organism, and a reflex analyzer having machine readable instructions stored in the memory that, when executed by the processor, control the processor to: receive stimuli data from the first sensor, receive EMG data from the second sensor, receive motion data from the third sensor, and process the stimuli data, the EMG data, and the motion data to determine one or both of a motion signature and an EMG signature and to generate a quantitative evaluation of the reflex response.

(K) In the system denoted as (J), the reflex analyzer may further comprise machine readable instructions stored in the memory that, when executed by the processor, control the processor to compare one of the motion signature and the EMG signature to a corresponding one of a previously captured motion signature and a previously captured EMG signature, to generate the quantitative evaluation of the reflex response.

(L) In either of the systems denoted as (J) and (K), the reflex analyzer may further comprise machine readable instructions stored in the memory that, when executed by the processor, control the processor to compare one of the motion signature and the EMG signature to a corresponding one of a reference motion signature and a reference EMG signature to generate the quantitative evaluation of the reflex response.

(M) In any of the systems denoted as (J)-(L), the motion signature may define a three-dimensional movement of the limb/appendage.

(N) In any of the systems denoted as (J)-(M), the reflex analyzer may further include machine readable instructions stored in the memory that, when executed by the processor, control the processor to determine a time of stimulation from the stimuli data, and to reference the motion signature and the EMG signature to the time of stimulation.

(O) In any of the systems denoted as (J)-(N), the first sensor may include at least three accelerometers for measuring three-dimensional acceleration of movement of the stimulating device, and the third sensor may include at least three accelerometers for quantitatively measuring three-dimensional acceleration of the limb/appendage.

(P) In any of the systems denoted as (J)-(0), the second sensor may comprise electrodes and conditioning electronics for detecting EMG signals.

(Q) Any of the systems denoted as (J)-(P), may further include an actuator coupled with the stimulating device and controlled by the processor to move the stimulating device to invoke the reflex response.

(R) Any of the systems denoted as (J)-(Q), may further include a display for displaying the quantitative evaluation of the reflex response to indicate health of the organism.

(S) In any of the systems denoted as (J)-(R), the stimulating device and the first sensor may be combined to form an intelligent stimulating device that controls and coordinates movement of the stimulating device.

(T) In any of the systems denoted as (J)-(S), the intelligent stimulating device may be configurable to induce a superficial reflex response.

(U) In any of the systems denoted as (J)-(T), the intelligent stimulating device may control the stimulating device to invoke the reflex response at a defined frequency.

(V) In any of the systems denoted as (J)-(U), the intelligent stimulating device may control the stimulating device to invoke the reflex response at a defined intensity.

(W) In any of the systems denoted as (J)-(V), the intelligent stimulating device may control the stimulating device to invoke the reflex response for a defined repeat count.

(X) In any of the systems denoted as (J)-(W), the intelligent stimulating device may communicate timing information to each of the second and third sensors.

(Y) In any of the systems denoted as (J)-(X), each of the motion signature and the EMG signature may include one or multiple components captured over time.

(Z) In any of the systems denoted as (J)-(Y), each of the motion signature and the EMG signature may include a quantitative depiction and rendition of the corresponding data, and/or a three-dimensional integration and/or depiction of this data as a motion envelope.

(AA) In any of the systems denoted as (J)-(Z), the motion signature and the EMG signature may form at least part of a heath care record that may be further refine using machine learning and big data.

What is claimed is:

1. A computer-implemented method for digital reflex quantization and signature analysis, comprising:
    capturing, from a first electronic sensor as stimuli data, a striking movement of a stimulating device invoking a reflex response in an organism;
    capturing, from a second electronic sensor as electromyographic (EMG) data, EMG of the reflex response;
    capturing, from a third electronic sensor as motion data, movement resulting from the reflex response of a limb/appendage of the organism;
    synchronizing the stimuli data, the EMG data, and the motion data;
    analyzing the stimuli data, the EMG data, and the motion data to determine one or both of a motion signature and an EMG signature comprising quantitative evaluation of the reflex response;
    detecting a reflex abnormality based on changes in the motion signature and the EMG signature over time; and
    displaying the quantitative evaluation of the reflex response to indicate health of the organism.

2. The computer-implemented method of claim 1, the step of detecting comprising comparing one of the motion signature and the EMG signature to a corresponding one of a previously captured motion signature and a previously captured EMG signature to detect the reflex abnormality.

3. The computer-implemented method of claim 1, the step of analyzing comprising comparing one of the motion signature and the EMG signature to a corresponding reference motion signature or reference EMG signature to detect the reflex abnormality.

4. The computer-implemented method of claim 3, further comprising matching one or both of the EMG signature and the motion signature to reference signatures corresponding to reflex responses for one or more diseases and/or disorders to diagnose a disease and/or disorder of the organism.

5. The computer-implemented method of claim 1, wherein the motion signature defines a three-dimensional movement of the limb/appendage and the stimuli data defines a time of stimulation, the motion signature and the EMG signature being referenced to the time of stimulation.

6. The computer-implemented method of claim 1, the quantitative evaluation being based at least in part upon three-dimensional acceleration of the limb/appendage quantitatively measured by at least three accelerometers configured with the limb/appendage.

7. The computer-implemented method of claim 1, the stimuli data comprising three-dimensional acceleration measurements of movement of the stimulating device.

8. The computer-implemented method of claim 1, further comprising controlling an actuator to generate the movement of the stimulating device to invoke the reflex response.

9. A system for digital reflex quantization and signature analysis, comprising:
    a processor;
    a non-transitory memory communicatively coupled with the processor;
    a first sensor configured to sense movement of a stimulating device invoking a reflex response in an organism;
    a second sensor configured to sense EMG of the reflex response;
    a third sensor configured to sense movement resulting from the reflex response of a limb/appendage of the organism; and
    a reflex analyzer software having machine readable instructions stored in the non-transitory memory that, when executed by the processor, control the processor to:
        receive stimuli data from the first sensor,
        receive EMG data from the second sensor,
        receive motion data from the third sensor,
        synchronize the stimuli data, the EMG data, and the motion data, and
        process the stimuli data, the EMG data, and the motion data to determine one or both of a motion signature and an EMG signature and to generate a quantitative evaluation of the reflex response, and detect a reflex abnormality based on changes in the motion signature and the EMG signature over time;

wherein the motion signature defines a three-dimensional movement of the limb/appendage.

10. The system of claim 9, the reflex analyzer software further comprising machine readable instructions stored in the non-transitory memory that, when executed by the processor, control the processor to compare one of the motion signature and the EMG signature to a corresponding one of a previously captured motion signature and a previously captured EMG signature, to detect the reflex abnormality.

11. The system of claim 9, the reflex analyzer software further comprising machine readable instructions stored in the non-transitory memory that, when executed by the processor, control the processor to compare one of the motion signature and the EMG signature to a corresponding one of a reference motion signature and a reference EMG signature to detect the reflex abnormality.

12. The system of claim 9, the reflex analyzer software further comprising machine readable instructions stored in the non-transitory memory that, when executed by the processor, control the processor to determine a time of stimulation from the stimuli data, and to synchronize the stimuli data, the EMG data, and the motion data by referencing the motion signature and the EMG signature to the time of stimulation.

13. The system of claim 9, the first sensor comprising at least three accelerometers for measuring three-dimensional acceleration of movement of the stimulating device, the second sensor comprising electrodes and conditioning electronics for detecting EMG signals, and the third sensor comprising at least three accelerometers for quantitatively measuring three-dimensional acceleration of the limb/appendage.

14. The system of claim 9, further comprising an actuator coupled with the stimulating device and controlled by the processor to move the stimulating device to invoke the reflex response.

15. The system of claim 9, further comprising a display for displaying the quantitative evaluation of the reflex response to indicate health of the organism.

16. The system of claim 9, the stimulating device and the first sensor being combined to form an intelligent stimulating device that controls and coordinates movement of the stimulating device and that is configurable to induce a superficial reflex response.

17. The system of claim 16, the intelligent stimulating device controlling the stimulating device to invoke the reflex response at one or more of a defined frequency, a defined intensity, and a defined repeat count.

18. The system of claim 16, the intelligent stimulating device communicating timing information to each of the second and third sensors.

19. The system of claim 9, each of the motion signature and the EMG signature comprising a quantitative depiction and rendition of the corresponding motion data and EMG data, and/or a three-dimensional integration and/or depiction of this data as a motion envelope.

20. The system of claim 9, the motion signature and the EMG signature forming at least part of a heath care record that is further refined using machine learning and big data.

* * * * *